United States Patent
Hong (10) Patent No.: US 11,266,367 B2
(45) Date of Patent: Mar. 8, 2022

(54) MAMMOGRAPHY DEVICE

(71) Applicant: VIEWORKS CO., LTD., Anyang-si (KR)

(72) Inventor: Soon Gil Hong, Cheonan-si (KR)

(73) Assignee: VIEWORKS CO., LTD., Anyang-si (KR)

( * ) Notice: Subject to any disclaimer, the term of this patent is extended or adjusted under 35 U.S.C. 154(b) by 0 days.

(21) Appl. No.: 17/133,739

(22) Filed: Dec. 24, 2020

(65) Prior Publication Data

US 2021/0204893 A1    Jul. 8, 2021

(30) Foreign Application Priority Data

Jan. 6, 2020 (KR) .................. 10-2020-0001330

(51) Int. Cl.
*A61B 6/00* (2006.01)
*A61B 6/04* (2006.01)
*A61B 6/10* (2006.01)

(52) U.S. Cl.
CPC ............ *A61B 6/502* (2013.01); *A61B 6/0414* (2013.01); *A61B 6/105* (2013.01); *A61B 6/4441* (2013.01)

(58) Field of Classification Search
CPC ........ A61B 6/502; A61B 6/0414; A61B 6/105
See application file for complete search history.

(56) References Cited

U.S. PATENT DOCUMENTS

2015/0320368 A1    11/2015   Lee et al.
2019/0150866 A1*    5/2019   Hong .................. A61B 6/502

FOREIGN PATENT DOCUMENTS

| EP | 2740406 A1 | 6/2014 |
| KR | 1020040013643 A | 2/2004 |
| KR | 100767111 B1 | 10/2007 |
| KR | 1020130077793 A | 7/2013 |
| KR | 1020190040521 A | 4/2019 |
| KR | 1020190056893 A | 5/2019 |
| WO | 2019074286 A1 | 4/2019 |

OTHER PUBLICATIONS

Extended European Search Report dated May 26, 2021.

* cited by examiner

*Primary Examiner* — Dani Fox
(74) *Attorney, Agent, or Firm* — Rabin & Berdo, P.C.

(57) ABSTRACT

Provided is a mammography device including: a C-arm including an irradiation unit configured to emit radioactive rays to a subject, and a detection unit on which the subject is disposed; a compression paddle coupled to the C-arm and configured to compress the subject; a carrying unit configured to move the compression paddle upward or downward; a drive unit configured to transmit power to the carrying unit; a belt support unit coupled to an upper portion of a main body of the C-arm and configured to support one side of a belt that operates in conjunction with an operation of the carrying unit; and a fall prevention unit coupled to one side of the belt support unit and configured to restrict an operation of the belt support unit when a rotation angle of the C-arm is a predetermined angle or more.

10 Claims, 9 Drawing Sheets

MAMMOGRAPHY DEVICE

CROSS-REFERENCE TO RELATED APPLICATIONS

This application claims priority to and the benefit of Korean Patent Application No. 10-2020-0001330 filed in the Korean Intellectual Property Office on Jan. 6, 2020, the entire contents of which are incorporated herein by reference.

TECHNICAL FIELD

The present invention relates to a mammography device, and more particularly, to a mammography device capable of preventing a paddle from falling in the event of an emergency shutdown or power failure.

BACKGROUND ART

In general, mammography has various advantages of radiography, specifically, X-ray imaging technology and has a unique feature that may minimize the exposure by enlarging images, reducing the number of image capturing processes, increasing the resolution, and adjusting the brightness and contrast ratio, as a result of which the use of mammography is rapidly growing.

A mammography device includes a main body disposed perpendicular to a floor and having a column shape, a C-arm having a middle part connected to the main body so as to be rotatable and movable upward and downward along the main body, the C-arm having a C shape or a shape similar thereto as a whole by being bent in an arc shape so that two opposite ends thereof face each other, an X-ray emitting unit mounted at one end of the C-arm and configured to emit X-rays toward the other end of the C-arm that faces one end of the C-arm, a detector facing the X-ray emitting unit, and a compression paddle configured to rectilinearly reciprocate along an inner surface of the C-arm between the X-ray emitting unit and the detector.

The compression paddle is moved upward or downward by a drive unit and applies pressure directly to a measurement subject, specifically, a breast with a load set based on an electrical signal.

Korean Patent Application Laid-Open No. 10-2019-0056893 discloses a mammography device capable of preventing a compression paddle from moving or falling to a subject and easily releasing the compression paddle pressing the subject in the event of an emergency such as a situation in which a supply of power is cut off.

SUMMARY OF THE INVENTION

The related art discloses a structure that prevents the compression paddle from falling in the event of an emergency in a state in which a C-arm is placed at an exact position (in a state in which an X-ray emitting unit is placed at an upper side and a detector is placed at a lower side). However, the related art does not consider a situation in which the compression paddle freely falls in the event of an emergency, such as a situation in which a supply of power is cut off, in a state in which the C-arm is placed at an inverted position (in a state in which the C-arm is rotated so that the detector is positioned at the upper side and the X-ray emitting unit is positioned at the lower side).

Accordingly, an object of the present invention is to provide a mammography device that prevents a fall of a compression paddle even in a state in which a rotation angle of the C-arm exceeds a predetermined angle range or larger, thereby preventing a structure of the mammography device from being damaged due to a sudden fall of the compression paddle.

An exemplary embodiment of the present invention provides a mammography device including: a C-arm including an irradiation unit configured to emit radioactive rays to a subject, and a detection unit on which the subject is disposed; a compression paddle coupled to the C-arm and configured to compress the subject; a carrying unit configured to move the compression paddle upward or downward; a drive unit configured to transmit power to the carrying unit; a belt support unit coupled to an upper portion of a main body of the C-arm and configured to support one side of a belt that operates in conjunction with an operation of the carrying unit; and a fall prevention unit coupled to one side of the belt support unit and configured to restrict an operation of the belt support unit when a rotation angle of the C-arm is a predetermined angle or more.

In particular, the fall prevention unit may include: a braking unit configured to stop the operation of the belt support unit when a supply of power to the mammography device is cut off; a swing gear unit configured to operate in conjunction with the braking unit and restrict the operation of the belt support unit by coming into contact with the belt support unit when the rotation angle of the C-arm is the predetermined angle or more; and a contact controller configured to control the swing gear unit to bring the swing gear unit into contact with the belt support unit when the rotation angle of the C-arm is the predetermined angle or more.

In particular, the belt support unit may include: a belt pulley support part coupled to the main body; a belt pulley coupled to one side of the belt pulley support part; and a belt gear axially coupled to the belt pulley through a rotary shaft at the other side of the belt pulley support part.

In particular, the braking unit may include: a braking unit support part coupled to the main body; a brake coupled to one side of the braking unit support part; and a braking gear axially coupled to the brake through a braking shaft at the other side of the braking unit support part.

In particular, the swing gear unit may include: a swing gear unit support part coupled to the other side of the braking unit support part and axially coupled to the braking gear through the braking shaft; a swing gear coupled in the swing gear unit support part and axially coupled to the swing gear unit support part through a swing gear shaft; and a first fastener provided at one side of the swing gear unit support part, in which when the rotation angle of the C-arm is the predetermined angle or more, the swing gear engages with the braking gear and rotates about the braking shaft, and the swing gear and the belt gear engage with each other.

In particular, the swing gear may be disposed to be spaced apart from the belt gear when the rotation angle of the C-arm is less than the predetermined angle.

In particular, a spring support part may be coupled to a front side of the braking unit support part, a second fastener may be provided at one side of the spring support part, a lower portion of a spring may be fastened to the first fastener, and an upper portion of the spring may be fastened to the second fastener.

In particular, the contact controller may be axially coupled to the braking unit support part.

In particular, when the rotation angle of the C-arm is the predetermined angle or more, the contact controller may be separated from the swing gear unit support part by rotating about a shaft connected to the braking unit support part and may control the swing gear to bring the swing gear into contact with the belt gear.

In particular, when the rotation angle of the C-arm is the predetermined angle or more, the spring may provide elastic force so that the swing gear comes into contact with the belt gear.

In particular, a rotation direction of the swing gear and a rotation direction of the belt gear may be opposite to each other when the swing gear and the belt gear engage with each other.

According to the exemplary embodiment of the present invention, it is possible to prevent the fall of the compression paddle even in the state in which the rotation angle of the C-arm exceeds a predetermined angle range or larger, thereby preventing the structure from being damaged due to a sudden fall of the compression paddle.

The foregoing summary is illustrative only and is not intended to be in any way limiting. In addition to the illustrative aspects, embodiments, and features described above, further aspects, embodiments, and features will become apparent by reference to the drawings and the following detailed description.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings. First, in assigning reference numerals to constituent elements of the respective drawings, it should be noted that the same constituent elements will be designated by the same reference numerals, if possible, even though the constituent elements are illustrated in different drawings. In addition, in the description of the present invention, the specific descriptions of publicly-known related configurations or functions will be omitted when it is determined that the specific descriptions may obscure the subject matter of the present invention. Further, the exemplary embodiments of the present invention will be described below, but the technical spirit of the present invention is not limited thereto and may of course be modified and variously carried out by those skilled in the art.

Figure 1A:
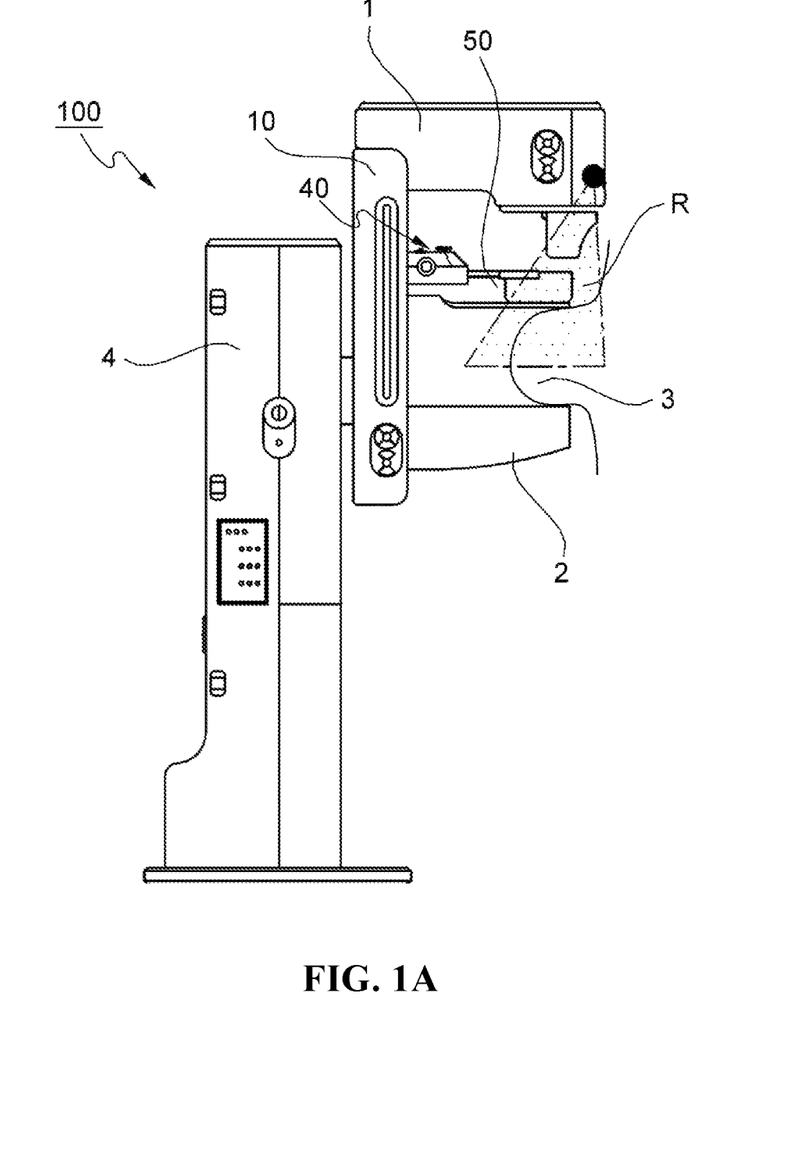
FIGS. 1A and 1B are views exemplarily illustrating a mammography device according to an exemplary embodiment of the present invention.
Figure 1B:
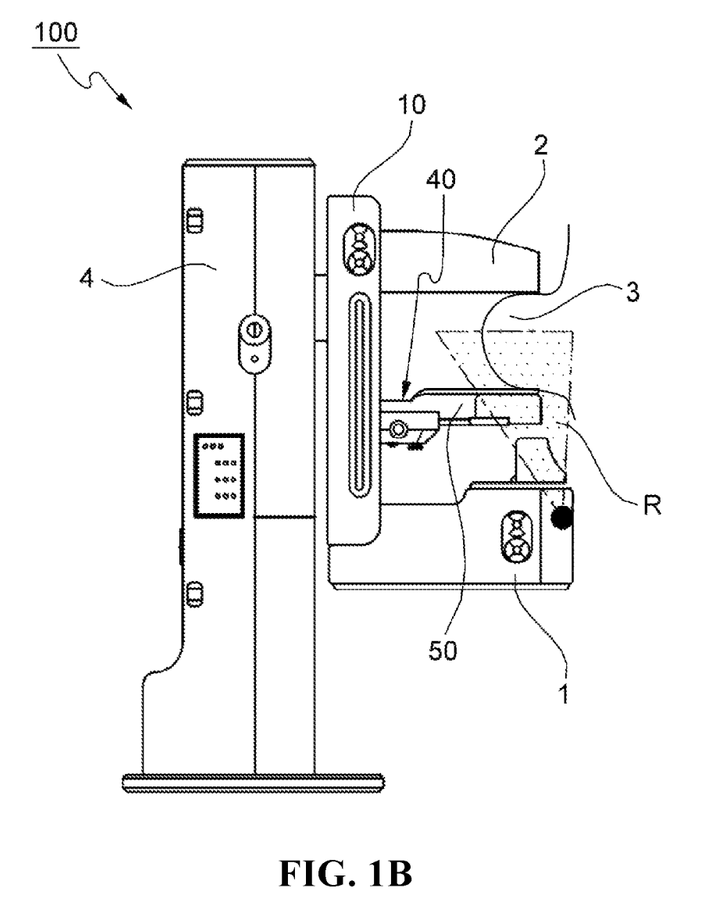

FIGS. 1A and 1B is a view exemplarily illustrating a mammography device 100 according to an exemplary embodiment of the present invention.

FIG. 1A illustrates a shape of a mammography device 100 when viewed from the lateral side.

As illustrated in FIG. 1A, the mammography device 100 includes an irradiation unit 1, a lifting unit 40, a detection unit 2, and a C-arm having an "alphabet C" shape and coupled to one side of a C-arm support unit 4.

the lifting unit 40 coupled to one side of a main body 10 of the C-arm and a compression paddle 50 coupled to one side of the lifting unit 40 and configured to compress a subject 3, may be coupled to the C-arm. The C-arm may be rotated in a state in which the C-arm is supported by the C-arm support unit 4.

As illustrated in FIG. 1A, the irradiation unit 1 of the mammography device 100 may emit radioactive rays R to the subject 3 disposed on the detection unit 2.

In this case, the irradiation unit 1 may be an X-ray emitting unit configured to emit X-rays, and the subject 3 may be a human breast. The X-rays may be used as the radioactive rays R, but the present invention is not limited thereto, and various modifications such as gamma rays may be used within a range in which the various modification can be used for medical purpose.

As the lifting unit 40 coupled to one side of the main body 10 is moved downward, the compression paddle 50 coupled to the lifting unit 40 may press the subject 3.

Meanwhile, in a state in which the C-arm is placed at an exact position as illustrated in FIG. 1A, the irradiation unit 1 may be positioned at the upper side and the detection unit 2 may be positioned at the lower side. In addition, in a state in which the C-arm is placed at an inverted position as illustrated in FIG. 1B, the C-arm may be rotated about a shaft (not illustrated) connected to the C-arm support unit 4 so that the detection unit 2 is positioned at the upper side and the irradiation unit 1 is positioned at the lower side.

Hereinafter, in the exemplary embodiment of the present invention, a configuration capable of preventing the compression paddle 50 from freely falling in a situation such as a situation in which a supply of power is cut off in the state illustrated in FIG. 1B will be described in detail.

Figure 2:
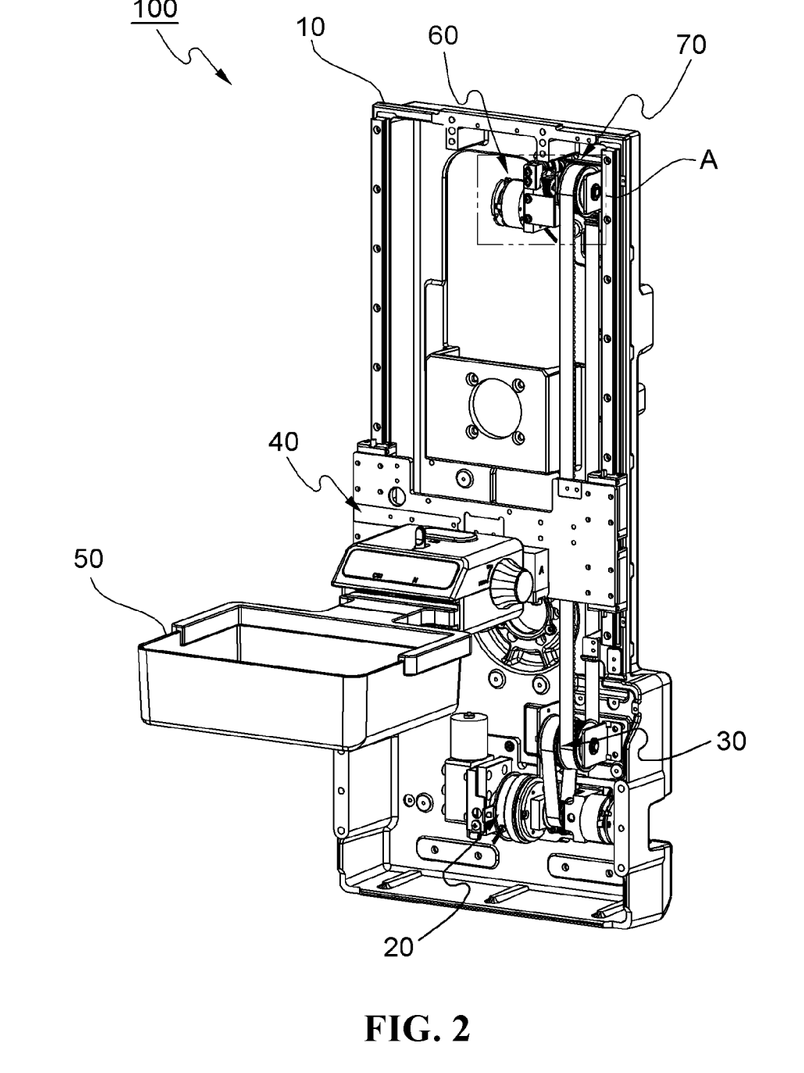
FIG. 2 is a view illustrating some components of the mammography device illustrated in FIGS. 1A and 1B.
Figure 3:
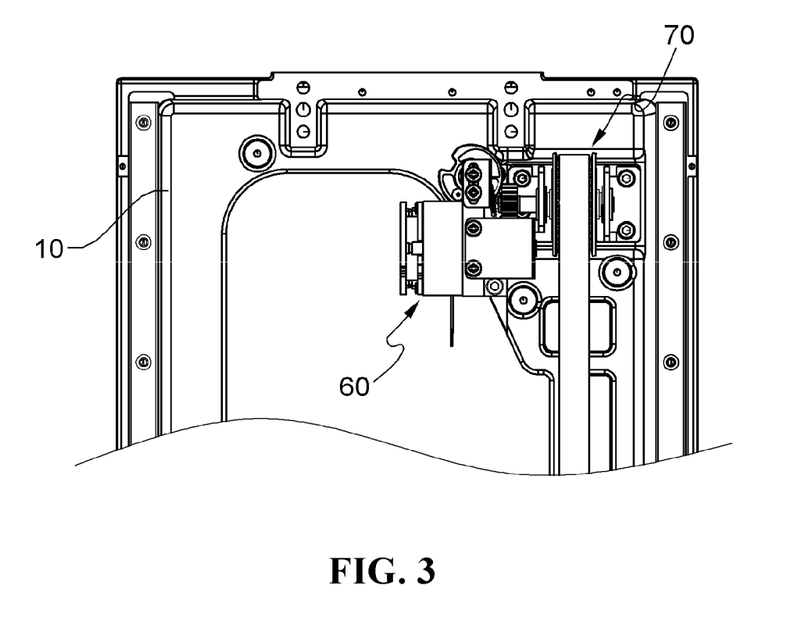
FIG. 3 is a view illustrating a specific part of the mammography device illustrated in FIG. 2 when viewed from the front side.
Figure 4A:
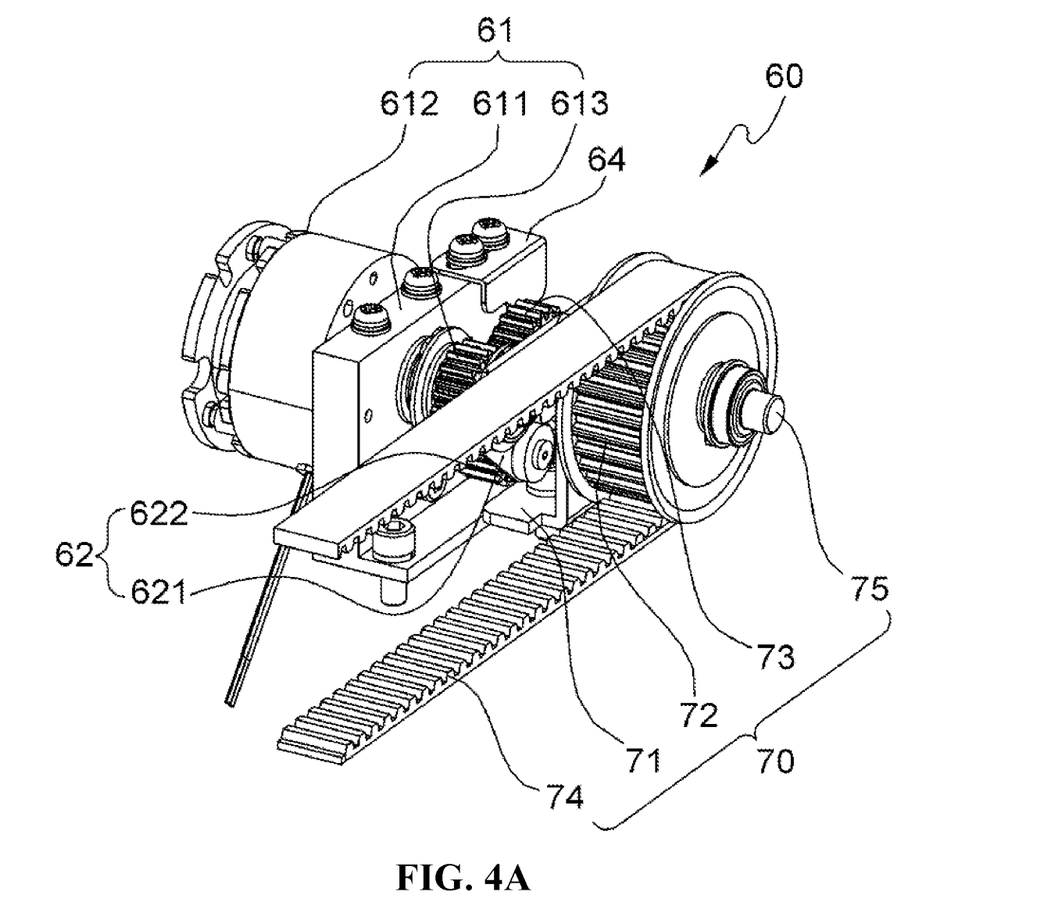
FIGS. 4A and 4B are enlarged views of part A illustrated in FIG. 2 when viewed from the upper and lower sides (the views illustrating a fall prevention unit according to the exemplary embodiment of the present invention).
Figure 4B:
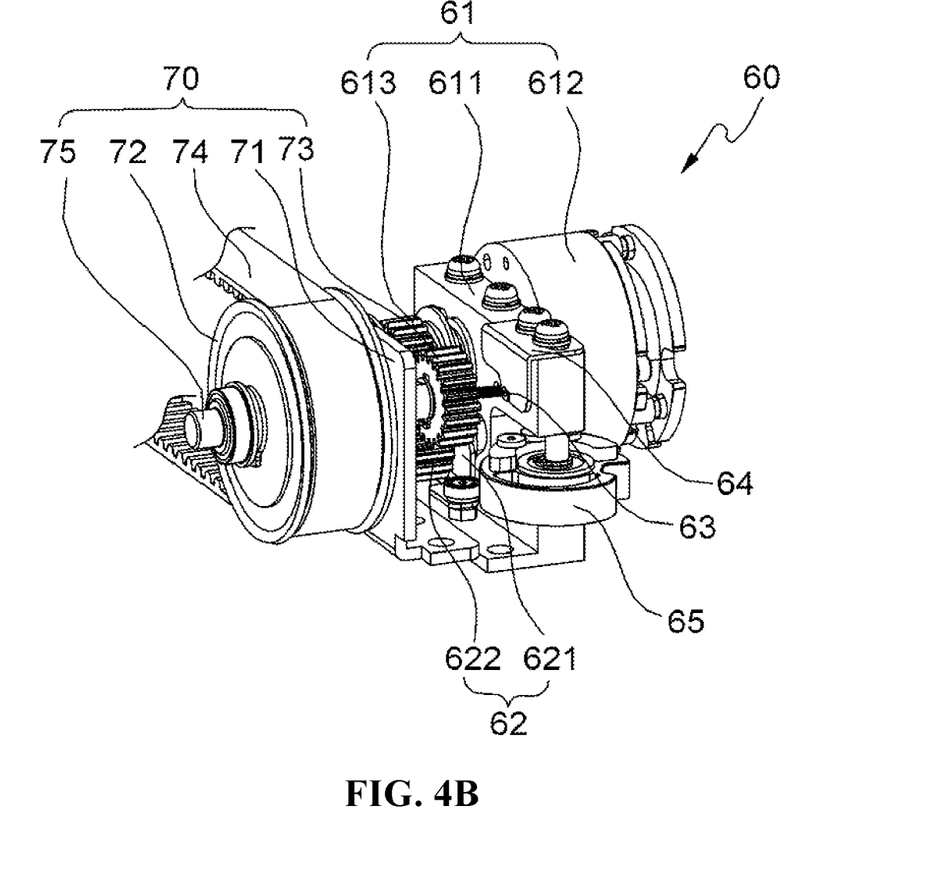
Figure 5:
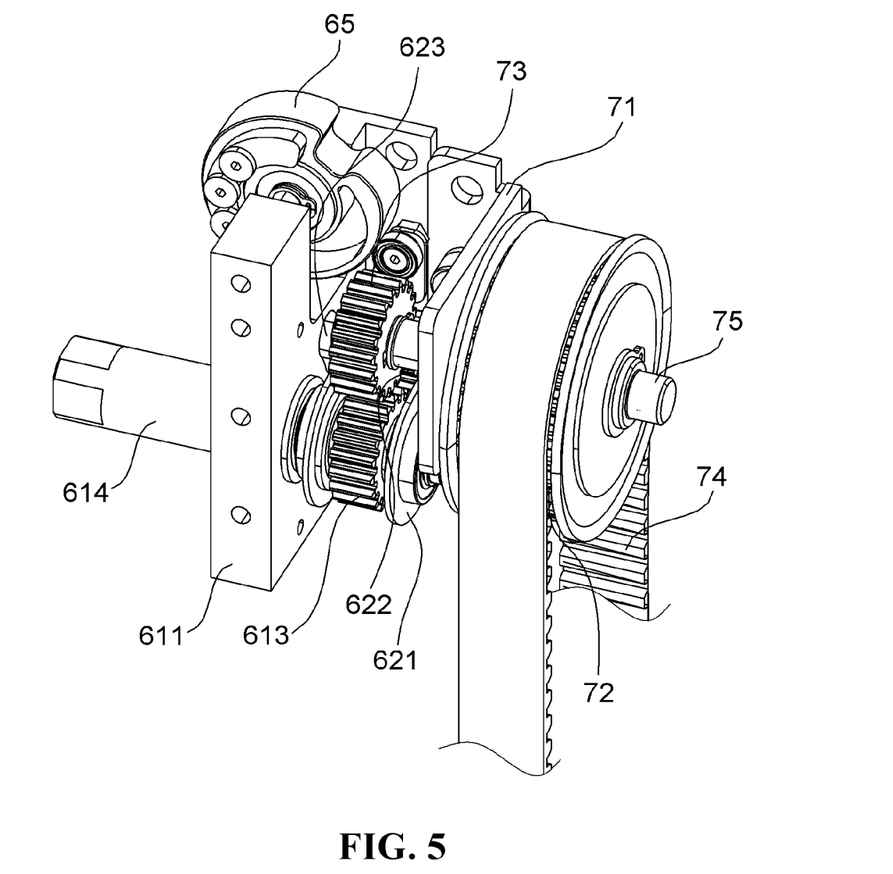
FIG. 5 is an enlarged view of part A illustrated in FIG. 2 when viewed from the front side (the view illustrating the fall prevention unit according to the exemplary embodiment of the present invention).
Figure 6A:
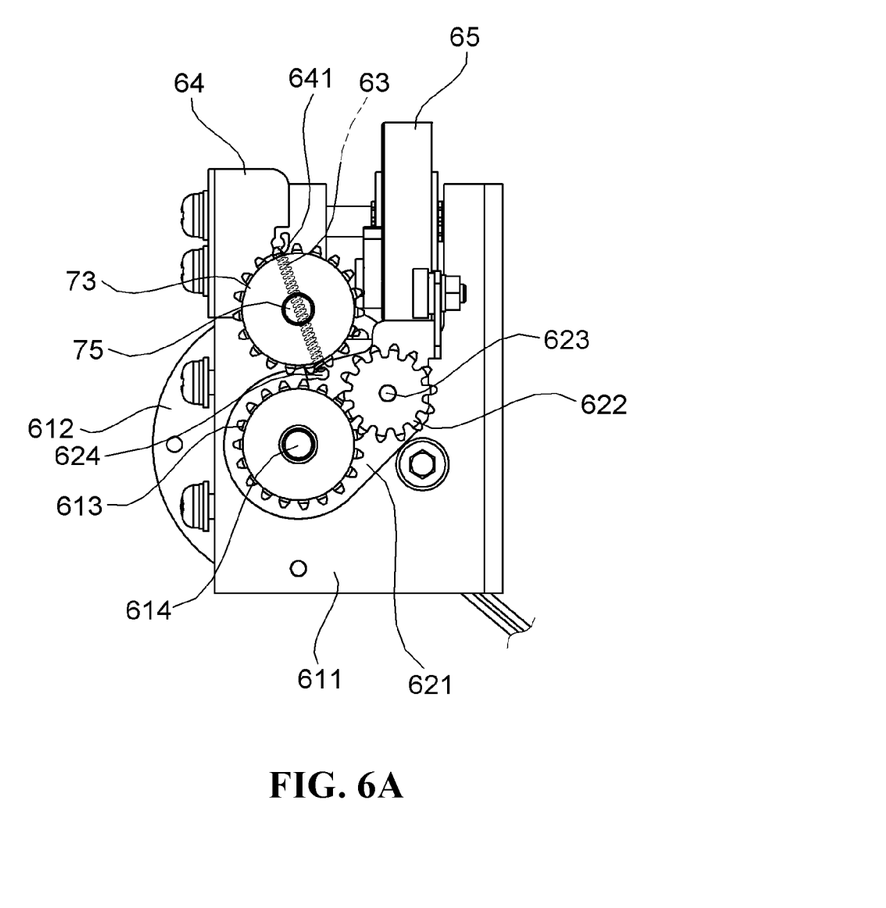
FIGS. 6A and 6B are views illustrating a state in which the fall prevention unit according to the exemplary embodiment of the present invention operates.
Figure 6B:
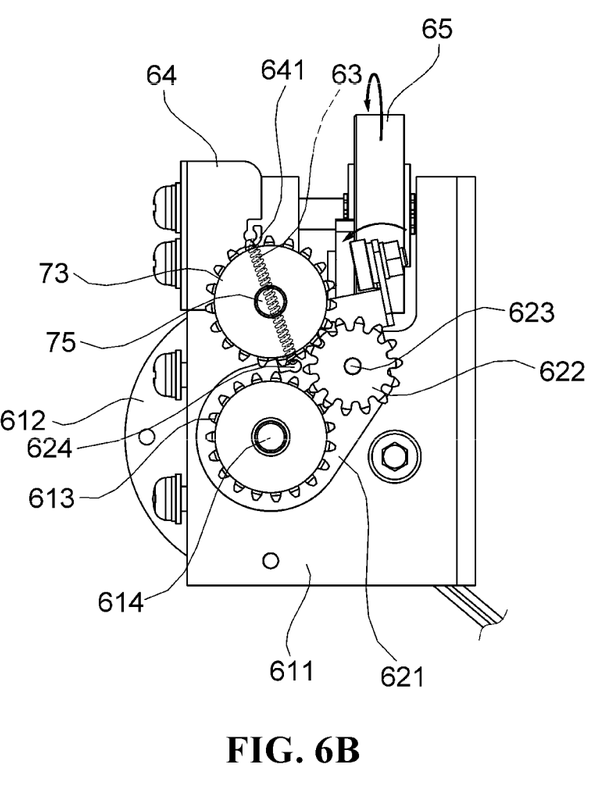

FIG. 2 is a view illustrating some components of the mammography device 100 illustrated in FIGS. 1A and 1B, FIG. 3 is a view illustrating a specific part of the mammography device 100 according to the exemplary embodiment of the present invention when viewed from the front side, FIGS. 4A and 4B are enlarged views of part A illustrated in FIG. 2 when viewed from the upper and lower sides (the views illustrating a fall prevention unit 60 according to the exemplary embodiment of the present invention), FIG. 5 is an enlarged view of part A illustrated in FIG. 2 (the view illustrating the fall prevention unit 60 according to the exemplary embodiment of the present invention), and FIGS. 6A and 6B are views illustrating a state in which the fall prevention unit 60 according to the exemplary embodiment of the present invention operates. In this case, some components of the fall prevention unit 60 to be described below are omitted from FIG. 5, and some components of a belt support unit 70 to be described below are omitted from FIG. 6.

Referring to FIG. 2, the mammography device 100 according to the exemplary embodiment of the present invention may include the compression paddle 50 configured to compress the subject 3, a carrying unit 30 configured to move the compression paddle 50 upward or downward, and a drive unit 20 configured to transmit power to the carrying unit 30.

In this case, the irradiation unit 1, the detection unit 2, the subject 3, and the C-arm support unit 4, which are described above, are omitted from FIG. 2.

Although not described in detail in the exemplary embodiment of the present invention, the drive unit 20 may include a drive motor connected to an external power source, and a driving shaft configured to be rotated by power transmitted from the drive motor. In addition, the power to be transmitted to the carrying unit 30 from the drive unit 20 may be, but not limited to, rotational power.

The carrying unit 30 may be rotated forward or reversely as the power is transmitted to the carrying unit 30 from the drive unit 20. As the carrying unit 30 is rotated forward or reversely, the lifting unit 40 connected to the carrying unit 30 may be moved in an up-down direction with respect to the main body 10 (e.g., the lifting unit 40 moves upward when the carrying unit 30 rotates forward). Therefore, the compression paddle 50 coupled to one side of the lifting unit 40 may be moved in the up-down direction with respect to the main body 10, such that the compression paddle 50 may compress the subject 3 or may be separated from the subject 3.

Meanwhile, the belt support unit 70 may be provided at an upper portion of the main body 10, and the belt support unit 70 supports one side of a belt 74 that operates in conjunction with an operation of the carrying unit 30.

In particular, as illustrated in FIGS. 4A, 4B and 5, the belt support unit 70 may include a belt pulley support part 71 coupled to the main body 10, a belt pulley 72 coupled to one side of the belt pulley support part 71, and a belt gear 73 axially coupled to the belt pulley 72 through a rotary shaft 75 at the other side of the belt pulley support part 71.

In this case, as the carrying unit 30 is rotated forward or reversely, the belt pulley 72 may also be rotated forward or reversely. When the belt pulley 72 is rotated, a carrying pulley (not illustrated) of the carrying unit 30 and the belt 74 disposed on the belt pulley 72 may be rotated about the carrying pulley and the belt pulley 72, which are rotation return points, as illustrated in FIGS. 2, 4A, 4B and 5. As a result, the compression paddle 50 may be moved upward or downward.

Meanwhile, when an emergency shutdown or power failure occurs and a supply of power to the mammography device 100 is cut off in the state in which the C-arm of the mammography device 100 is rotated (for example, a state in which a rotation angle of the C-arm is 180° based on a normal position illustrated in FIG. 1A), as illustrated in FIG. 1B, the compression paddle 50 may freely fall due to weight of the components connected to the compression paddle 50, which may cause damage to the components such as the irradiation unit 1 and also cause a risk of damage to the compression paddle 50.

In this regard, in the exemplary embodiment of the present invention, as illustrated in FIGS. 2, and 3 to 5, the mammography device 100 may further include the fall prevention unit 60 coupled to one side of the belt support unit 70 and configured to restrict the operation of the belt support unit 70 when the rotation angle of the C-arm is a predetermined angle or more.

In this case, a range of rotation angle of the C-arm, in which the fall prevention unit 60 operates to restrict the operation of the belt support unit 70, may be 160° or more and less than 180° based on the normal position (0°) illustrated in FIG. 1A.

However, the present invention is not limited thereto, and the fall prevention unit 60 may be set to operate within a range of rotation angle of the C-arm in which the compression paddle 50 may freely fall due to weight of the components connected to the compression paddle 50.

The fall prevention unit 60 may include a braking unit 61 that stops the operation of the belt support unit 70 when a supply of power to the mammography device 100 is cut off.

In this case, as illustrated in FIGS. 4A, 4B and 5, the braking unit 61 may include a braking unit support part 611 coupled to the main body 10, a brake 612 coupled to one side of the braking unit support part 611, and a braking gear 613 axially coupled to the brake 612 through a braking shaft 614 at the other side of the braking unit support part 611.

The brake 612 may be a kind of electronic brake, and particularly, may be a demagnetized brake that generates braking force using pressure of an embedded spring when power is cut off in an emergency situation such as power failure.

In this case, the brake 612 may slip if physical force higher than braking force of the brake 612 is applied. In addition, when braking force is generated by the brake 612, the braking gear 613, together with the braking shaft 614, may be braked.

The fall prevention unit 60 may further include a swing gear unit 62 configured to operate in conjunction with the braking unit 61 and restrict the operation of the belt support unit 70 by coming into contact with the belt support unit 70 when the rotation angle of the C-arm is a predetermined angle or more, and a contact controller 65 configured to control the swing gear unit 62 to bring the swing gear unit 62 into contact with the belt support unit 70 when the rotation angle of the C-arm is the predetermined angle or more.

As illustrated in FIGS. 4A, 4B, 5 and 6, the swing gear unit 62 may include a swing gear unit support part 621 coupled to the other side of the braking unit support part 611 and axially coupled to the braking gear 613 through the braking shaft 614, a swing gear 622 coupled in the swing gear unit support part 621 and axially coupled to the swing gear unit support part 621 through the swing gear shaft 623, and a first fastener 624 provided at one side of the swing gear unit support part 621.

In this case, as illustrated in FIGS. 4A, 4B and 5, the braking gear 613 and the swing gear 622 may be coupled and supported in the swing gear unit support part 621.

A lower portion of a spring 63 to be described below may be fastened to the first fastener 624. Further, a spring support part 64 may be coupled to a front side of the braking unit support part 611, a second fastener 641 may be provided at one side of the spring support part 64, and an upper portion of the spring 63 may be fastened to the second fastener 641.

Meanwhile, in a case in which the rotation angle of the C-arm is less than the predetermined angle and power is normally applied to the mammography device 100, the swing gear 622 may be disposed to be spaced apart from the belt gear 73 of the belt support unit 70 at a predetermined interval, as illustrated in FIG. 6A.

In contrast, when the supply of power to the mammography device 100 is cut off in the event of an emergency shutdown or power failure, braking force is generated by the brake 612, such that the braking gear 613 rotates about the braking shaft 614. In this case, as illustrated in FIG. 6B, the swing gear 622 may engage with the braking gear 613 and rotate about the braking shaft 614 connected to the braking gear 613. In this case, a rotation direction of the braking gear 613 and a rotation direction of the swing gear 622 are opposite to each other.

Meanwhile, as described above, when the rotation angle of the C-arm is the predetermined angle or more, the contact controller 65 may control the swing gear unit 62 to bring the swing gear unit 62 into contact with the belt support unit 70. In this case, as illustrated in FIGS. 4A, 4B and 5, the contact controller 65 may be axially coupled between the front side and the rear side of the braking unit support part 611 and may be an electronic solenoid.

As illustrated in FIGS. 4A, 4B and 6A, when the rotation angle of the C-arm is less than the predetermined angle, the contact controller 65 may come into contact with the swing gear unit support part 621, particularly, an end of the swing gear unit support part 621.

As illustrated in FIG. 6A, the contact controller 65 does not rotate when the mammography device 100 normally operates. However, as illustrated in FIG. 6B, when the C-arm rotates by a predetermined rotation angle or more, the contact controller 65 may control the swing gear 622 to bring the swing gear 622 into contact with the belt gear 73 of the belt support unit 70. In this case, a center of gravity of the contact controller 65 may always be directed toward the ground surface in a gravitational direction.

In particular, when the supply of power to the mammography device 100 is cut off and the C-arm is rotated by the predetermined rotation angle or more in the event of an emergency shutdown or power failure, braking force is generated by the brake 612 of the braking unit 61, such that the braking gear 613 may be braked. Further, the swing gear 622 may engage with the braking gear 613 and rotate about the braking shaft 614 connected to the braking gear 613.

In this case, as illustrated in FIG. 6B, the contact controller 65 may rotate about a shaft connected to the braking unit support part 611. In this case, as the contact controller 65 rotates, the contact controller 65 and the end of the swing gear unit support part 621 are separated from each other, such that the restriction to the swing gear unit support part 621 is released, and as a result, the swing gear unit support part 621 may be inclined in a direction of the belt gear 73.

Therefore, the swing gear 622 approaches the belt gear 73, and the spring 63 vertically fastened to the first fastener 624 and the second fastener 641 is compressed, thereby providing elastic force so that the swing gear 622 may come into contact with the belt gear 73.

In particular, the spring 63 may be a tensile spring lighter in weight than the swing gear 622. When the rotation angle of the C-arm is the predetermined angle or more (e.g., 160° or more and less than 180°) the spring 63 may provide tensile force to improve contact characteristics between the swing gear 622 and the belt gear 73. In this case, as a load of the swing gear 622 is additionally applied, contact characteristics between the swing gear 622 and the belt gear 73 may further be improved.

When the swing gear 622 is in contact with the belt gear 73, the swing gear 622 and the belt gear 73 may engage with each other. In this case, a rotation direction of the swing gear 622 and a rotation direction of the belt gear 73 are opposite to each other, and as described above, the rotation direction of the braking gear 613 and the rotation direction of the swing gear 622 are opposite to each other.

Therefore, when the supply of power to the mammography device 100 is cut off and the C-arm is rotated by the predetermined rotation angle or more in the event of an emergency shutdown or power failure, braking force may be generated by the brake 612 of the braking unit 61, and thus braking force may be applied to the braking gear 613. In this case, as illustrated in FIG. 6B, the belt gear 73 and the swing gear 622 may come into contact and engage with each other, such that the rotation of the belt gear 73 may be stopped.

Therefore, the rotation of the belt pulley 72 axially coupled to the belt gear 73 through the rotary shaft 75 is also stopped, and thus the movement of the compression paddle 50 is stopped. As a result, it is possible to prevent the fall of the compression paddle 50 in the event of an emergency even in the situation in which the supply of power to the mammography device 100 is cut off and the C-arm is rotated by the predetermined rotation angle or more in the event of an emergency shutdown or power failure, as illustrated in FIG. 1B.

In this case, when a user manually applies physical force, which is higher than braking force of the brake 612, to the compression paddle 50 (when the user applies force in a direction of the irradiation unit 1 based on FIG. 1B), the brake 612 may slip to separate the subject 3 from the compression paddle 50. In this case, when the rotation angle of the C-arm is the predetermined angle or more (e.g., 160° or more and less than 180°), a weight of the compression paddle 50 is additionally applied, such that the compression paddle 50 may be more easily released.

Meanwhile, when the rotation angle of the C-arm becomes less than the predetermined angle (e.g., less than 160°) in the state illustrated in FIG. 1B, the contact controller 65 may rotate in a direction opposite to the rotation direction illustrated in FIG. 6B.

In this case, unlike the case in which the rotation angle of the C-arm is the predetermined angle or more, the load of the swing gear 622 is less applied to the spring 63, such that tensile force lower than the load of the swing gear 622 is applied, and as a result, the spring 63 may be stretched. Therefore, the spring 63 vertically fastened to the first fastener 624 and the second fastener 641 returns back to an initial state, thereby providing elastic force so that the swing gear 622 may be separated from the belt gear 73.

As the spring 63 returns back to the initial state, the swing gear unit support part 621 returns to an original position in a direction away from the belt gear 73, as illustrated in FIG. 6A, such that the contact controller 65 and the end of the swing gear unit support part 621 may come into contact with each other again.

In this case, as illustrated in FIG. 6A, since the belt gear 73 and the swing gear 622 are separated from each other, the belt pulley 72 axially coupled to the belt gear 73 through the rotary shaft 75 may be rotated, and the compression paddle 50 may normally move upward or downward.

According to the exemplary embodiment of the present invention, it is possible to prevent the fall of the compression paddle even in the state in which the rotation angle of the C-arm exceeds a predetermined angle range or larger, thereby preventing the structure from being damaged due to a sudden fall of the compression paddle.

The above description is simply given for illustratively describing the technical spirit of the present invention, and those skilled in the art to which the present invention pertains will appreciate that various modifications, changes, and substitutions are possible without departing from the essential characteristic of the present invention. Accordingly, the exemplary embodiments disclosed in the present invention and the accompanying drawings are intended not to limit but to describe the technical spirit of the present invention, and the scope of the technical spirit of the present invention is not limited by the exemplary embodiments and the accompanying drawings. The protective scope of the present invention should be construed based on the following claims, and all the technical spirit within the equivalent scope thereto should be construed as falling within the scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A mammography device comprising:
   a C-arm comprising an irradiation unit configured to emit radioactive rays to a subject, and a detection unit on which the subject is disposed;
   a compression paddle coupled to the C-arm and configured to compress the subject;
   a carrying unit configured to move the compression paddle upward or downward;
   a drive unit configured to transmit power to the carrying unit;
   a belt support unit coupled to an upper portion of a main body of the C-arm and configured to support one side of a belt that operates in conjunction with an operation of the carrying unit; and
   a fall prevention unit coupled to one side of the belt support unit and configured to restrict an operation of the belt support unit when a rotation angle of the C-arm is a predetermined angle or more.

2. The mammography device of claim 1, wherein the fall prevention unit comprises:
   a braking unit configured to stop the operation of the belt support unit when a supply of power to the mammography device is cut off;
   a swing gear unit configured to operate in conjunction with the braking unit and restrict the operation of the belt support unit by coming into contact with the belt support unit when the rotation angle of the C-arm is the predetermined angle or more; and
   a contact controller configured to control the swing gear unit to bring the swing gear unit into contact with the belt support unit when the rotation angle of the C-arm is the predetermined angle or more, and
   wherein the belt support unit comprises:
   a belt pulley support part coupled to the main body;
   a belt pulley coupled to one side of the belt pulley support part; and
   a belt gear axially coupled to the belt pulley through a rotary shaft at the other side of the belt pulley support part.

3. The mammography device of claim 2, wherein the braking unit comprises:
   a braking unit support part coupled to the main body;
   a brake coupled to one side of the braking unit support part; and
   a braking gear axially coupled to the brake through a braking shaft at the other side of the braking unit support part.

4. The mammography device of claim 3, wherein the swing gear unit comprises:
   a swing gear unit support part coupled to the other side of the braking unit support part and axially coupled to the braking gear through the braking shaft;
   a swing gear coupled in the swing gear unit support part and axially coupled to the swing gear unit support part through a swing gear shaft; and
   a first fastener provided at one side of the swing gear unit support part, and
   wherein when the rotation angle of the C-arm is the predetermined angle or more, the swing gear engages with the braking gear and rotates about the braking shaft, and the swing gear and the belt gear engage with each other.

5. The mammography device of claim 4, wherein the swing gear is disposed to be spaced apart from the belt gear when the rotation angle of the C-arm is less than the predetermined angle.

6. The mammography device of claim 4, wherein a spring support part is coupled to a front side of the braking unit support part, a second fastener is provided at one side of the spring support part, a lower portion of a spring is fastened to the first fastener, and an upper portion of the spring is fastened to the second fastener.

7. The mammography device of claim 3, wherein the contact controller is axially coupled to the braking unit support part.

8. The mammography device of claim 4, wherein when the rotation angle of the C-arm is the predetermined angle or more, the contact controller is separated from the swing gear unit support part by rotating about a shaft connected to the braking unit support part and controls the swing gear to bring the swing gear into contact with the belt gear.

9. The mammography device of claim 6, wherein when the rotation angle of the C-arm is the predetermined angle or more, the spring provides elastic force so that the swing gear comes into contact with the belt gear.

10. The mammography device of claim 4, wherein a rotation direction of the swing gear and a rotation direction of the belt gear are opposite to each other when the swing gear and the belt gear engage with each other.

* * * * *